Dec. 21, 1954 F. C. CHANDLER Plant Pat. 1,330
RED VERBENA PLANT
Filed March 12, 1954
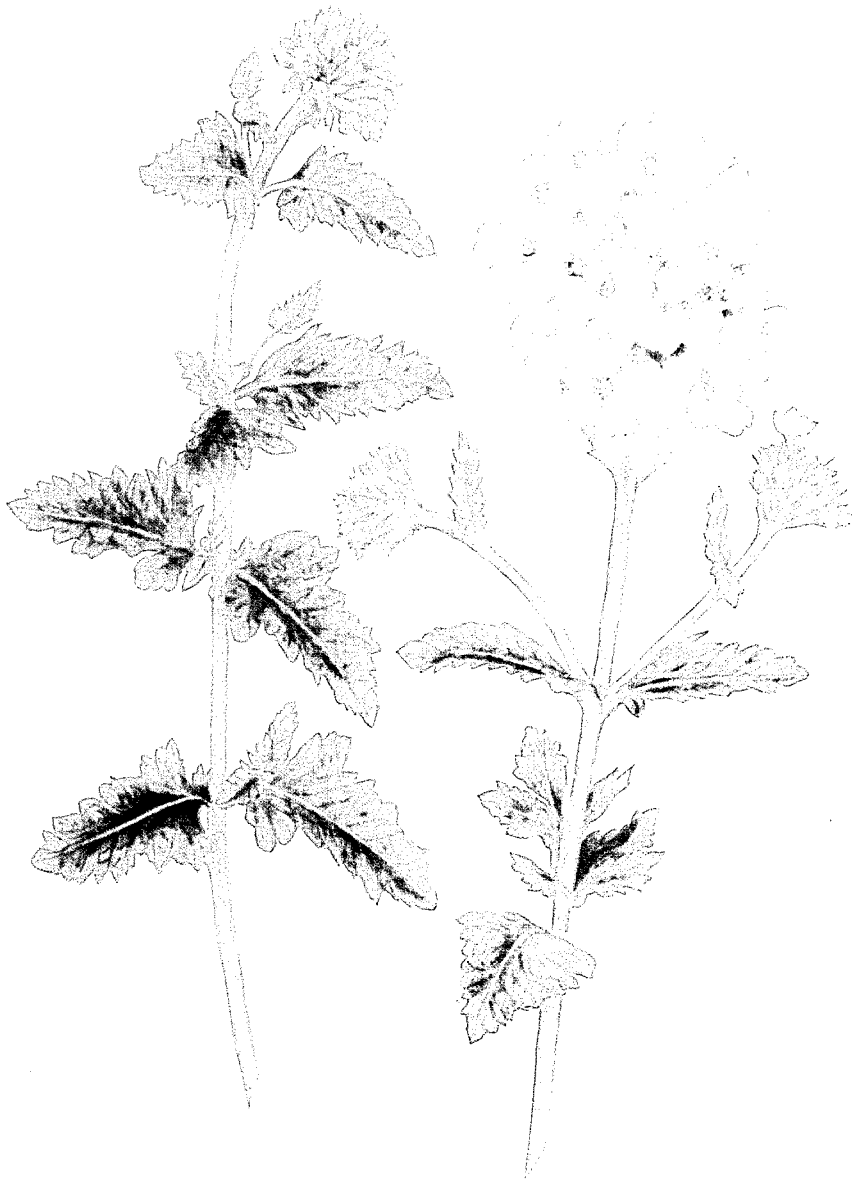
INVENTOR.
Florence Clyde Chandler
BY
Pennie, Edmonds Morton Barrows Taylor
ATTORNEYS United States Patent Office Plant Pat. 1,330
Patented Dec. 21, 1954

1,330

RED VERBENA PLANT

Florence Clyde Chandler, Ardsley, N. Y., assignor to Boyce Thompson Institute for Plant Research, Inc., Yonkers, N. Y., a corporation of New York Application March 12, 1954, Serial No. 415,992

1 Claim. (Cl. 47—60)

This invention provides a new and distinct variety of red verbena plant. The new variety of plant is particularly characterized by its unique spectrum red flowers which are exceptionally large forming large clusters of many flowers which are borne on long, stiff stems, by its large thick, dark green leaves which retain their color throughout the summer, by erect habit, and by good vigor. The new variety has been reproduced asexually from cuttings, and the characteristics appear to be fixed.

The distinct variety of red verbena was produced from seeds of *Verbena hybrida,* Hort. Spectrum Red, treated with colchicine for the induction of polyploidy. This plant so produced is a tetraploid with $2n=20$ chromosomes. The untreated plants of Spectrum Red are diploids with $2n=10$ chromosomes. The new variety of plant, as thus originated, was asexually reproduced from cuttings at Boyce Thompson Institute for Plant Research, Inc., Yonkers, New York. In the accompanying drawing a plant of the invention is illustrated by a painting of a mature plant in substantially full bloom.

*Flowers*

The flowers are distinct from all forms of Spectrum Red because the flower clusters are usually at least 2½ inches in diameter and 1¾ inches deep. Individual flowers are about 13/16 inch in diameter and are, according to Ridgway's "Color Standards and Nomenclature" published by the author from the press of A. Hoen and Company, Baltimore, Md., 1912, light carmine merging into spectrum red toward the margin. According to "Munsell Book of Color," published by Munsell Color Company, Inc., Baltimore, Md., 1929, the flowers are R 3/12 (Red hue, value 3, and chroma 12) and merge to R 4/14 at the margin. The general color is a rich bright red. There are usually 35–40 flowers per cluster which are borne on stiff stems about ⅛ inch in diameter and usually at least 12 inches long.

*Leaves*

The leaves are thick, dark green in color, and generally are about 1¼ inches in diameter and about 2 inches in length near the base, while the leaves at the tips of the branches are smaller.

*Seeds*

No seeds have been obtained from fully controlled self-pollinations. The anthers are small and green, pollen is pale yellow, 78 per cent of which is aborted. The plant must, therefore, be propagated vegetatively by means of cuttings which has been done without any difficulties. The largest pollen grains which are capable of germination are 47.5 to 76 microns in diameter. The number of chromosomes determined $2n=20$.

*General*

The new variety of plant is more vigorous and robust than the old variety of Spectrum Red verbena. The plant remains in good vegetative condition throughout the summer and the leaves remain green and do not burn during the summer. The plant flowers well and has a profusion of bloom throughout the summer and until killed by frost.

I claim:

A new and distinct variety of spectrum red verbena plant substantially as illustrated and described, characterized by large, bright red individual flowers in large clusters of many flowers borne on long, erect stems, by large, thick dark green leaves which retain their color through the summer, and by good vigor.

No references cited.